United States Patent
Song et al.

(10) Patent No.: US 11,826,324 B2
(45) Date of Patent: Nov. 28, 2023

(54) PHARMACEUTICAL COMPOSITIONS FOR PREVENTING OR TREATING INFLAMMATORY DISEASE, AUTOIMMUNE DISEASE, OR COMBINATION THEREOF, AND METHOD FOR USING SAME

(71) Applicants: INDUSTRY-ACADEMIC COOPERATION FOUNDATION, YONSEI UNIVERSITY, Seoul (KR); IMMUNOMET THERAPEUTICS INC., Houston, TX (US)

(72) Inventors: Jungsik Song, Seoul (KR); Beom Seok Kim, Seoul (KR); Sang Jun Ha, Seoul (KR); Ji Min Son, Seoul (KR)

(73) Assignees: INDUSTRY-ACADEMIC COOPERATION FOUNDATION, YONSEI UNIVERSITY, Seoul (KR); IMMUNOMET THERAPEUTICS INC., Houston, TX (US)

( * ) Notice: Subject to any disclaimer, the term of this patent is extended or adjusted under 35 U.S.C. 154(b) by 71 days.

(21) Appl. No.: 17/126,478

(22) Filed: Dec. 18, 2020

(65) Prior Publication Data
US 2021/0113497 A1    Apr. 22, 2021

Related U.S. Application Data

(63) Continuation of application No. 16/480,294, filed as application No. PCT/KR2018/000989 on Jan. 23, 2018, now abandoned.

(30) Foreign Application Priority Data

Jan. 24, 2017 (KR) .................. 10-2017-0011143

(51) Int. Cl.
*A61K 31/155* (2006.01)
*A61K 31/436* (2006.01)
*A61K 31/40* (2006.01)

(52) U.S. Cl.
CPC ............ *A61K 31/155* (2013.01); *A61K 31/40* (2013.01); *A61K 31/436* (2013.01)

(58) Field of Classification Search
None
See application file for complete search history.

(56) References Cited

U.S. PATENT DOCUMENTS

| | | | | |
|---|---|---|---|---|
| 9,321,742 B2 * | 4/2016 | Kim | ................ | C07D 333/20 |
| 9,539,238 B2 * | 1/2017 | Kang | ................ | A61K 31/495 |
| 9,540,325 B2 * | 1/2017 | Kim | ................ | A61P 15/08 |
| 9,884,821 B2 * | 2/2018 | Min | ................ | C07D 207/20 |
| 10,058,558 B2 * | 8/2018 | Kim | ................ | A61K 31/44 |
| 10,221,190 B2 * | 3/2019 | Kim | ................ | C07D 211/38 |
| 10,252,996 B2 * | 4/2019 | Min | ................ | C07D 211/16 |
| 10,590,081 B2 * | 3/2020 | Kim | ................ | A61P 35/00 |
| 10,626,085 B2 * | 4/2020 | Kim | ................ | C07D 211/10 |

OTHER PUBLICATIONS

Ju et al., "HL156A, a novel AMP-activated protein kinase activator, is protective against peritoneal fibrosis in an in vivo and in vitro model of peritoneal fibrosis", Mar. 2016, 310(5), pp. F342-F350. (doi.org/10.1152/ajprenal.00204.2015) (Year: 2016).*

Lee et al., "AMP-activated protein kinase activator, HL156A reduces thioacetamide-induced liver fibrosis in mice and inhibits the activation of cultured hepatic stellate cells and macrophages", Oct. 2016, International J. Oncology, 49(4), pp. 1407-1414. (doi.org/10.3892/ijo.2016.3627) (Year: 2016).*

* cited by examiner

*Primary Examiner* — My-Chau T. Tran
(74) *Attorney, Agent, or Firm* — Schwabe Williamson & Wyatt

(57) ABSTRACT

Provided are a pharmaceutical composition for preventing or treating inflammatory disease, autoimmune disease, graft rejection responses, or combinations thereof, the pharmaceutical composition including a compound represented by Formula 1, or a stereoisomer, derivative, solvate, or pharmaceutically acceptable salt thereof, and a method using the pharmaceutical composition. The pharmaceutical composition and the method can be used to effectively prevent or treat inflammatory disease, autoimmune disease, graft rejection responses, or combinations thereof.

8 Claims, 6 Drawing Sheets

PHARMACEUTICAL COMPOSITIONS FOR PREVENTING OR TREATING INFLAMMATORY DISEASE, AUTOIMMUNE DISEASE, OR COMBINATION THEREOF, AND METHOD FOR USING SAME

CROSS-REFERENCE TO RELATED APPLICATION

This patent application is a continuation of U.S. patent application Ser. No. 16/480,294, filed Jul. 23, 2019, entitled "PHARMACEUTICAL COMPOSITIONS FOR PREVENTING OR TREATING INFLAMMATORY DISEASE, AUTOIMMUNE DISEASE, OR COMBINATION THEREOF, AND METHOD FOR USING SAME", which is a U.S. National Phase Application under 35 U.S.C. § 371 of International Application No. PCT/KR2018/000989, filed Jan. 23, 2018, entitled "PHARMACEUTICAL COMPOSITIONS FOR PREVENTING OR TREATING INFLAMMATORY DISEASE, AUTOIMMUNE DISEASE, OR COMBINATION THEREOF, AND METHOD FOR USING SAME", which claims the benefit of Korean Application No. 10-2017-0011143, filed Jan. 24, 2017, entitled "PHARMACEUTICAL COMPOSITIONS FOR PREVENTING OR TREATING INFLAMMATORY DISEASE, AUTOIMMUNE DISEASE, OR COMBINATION THEREOF, AND METHOD FOR USING SAME," the entire contents of which are hereby incorporated by reference herein.

FIELD

The present disclosure relates to a pharmaceutical composition for preventing or treating inflammatory disease, autoimmune disease, or combinations thereof, the pharmaceutical composition including a phenylbiguanide derivative compound, or a stereoisomer, derivative, solvate, or pharmaceutically acceptable salt thereof, and a method using the pharmaceutical composition.

BACKGROUND ART

T lymphocytes are one type of white blood cells, accounting for about 30% of white blood cells. T lymphocytes can be sub-categorized as naive T lymphocytes, helper T lymphocytes, cytotoxic T lymphocytes, and memory T lymphocytes, and the like. Memory T lymphocytes are cells capable of being rapidly activated after long-term survival when an antigen, which has been recognized thereby, invades again. Secondary immune responses by memory T lymphocytes play an important role in immune response, but memory T lymphocytes may cause disease such as excessive immune response or autoimmune disease.

Inflammatory disease is a disease with inflammation manifesting as a major lesion and accompanied by various symptoms such as pain, fever and edema. Autoimmune disease develops when an immune cell attacks organs or tissues of the body, resulting in immune imbalance or loss of resistance to self-antigens. There is a need to suppress excessive immune responses to treat, for example, inflammatory disease and autoimmune disease.

As a biguanide derivative compound, an N1-cyclicamine-N5-substituted phenylbiguanide derivative compound has been known to have anticancer, anti-hyperglycemic and lipid lowering effects (Korean Patent Application Publication No. 10-2013-0019351). However, the effect of the N1-cyclicamine-N5-substituted phenylbiguanide derivative compound on the immune response was not known.

Therefore, to prevent or treat inflammatory disease, autoimmune disease, or combinations thereof, there is a need to study the function of the N1-cyclicamine-N5-substituted phenylbiguanide derivative compound in relation to the immune response.

DESCRIPTION OF EMBODIMENTS

Technical Problem

Provided are pharmaceutical compositions for preventing or treating inflammatory disease, autoimmune disease, or combinations thereof.

Provided are methods of preventing or treating inflammatory disease, autoimmune disease, or combinations thereof.

Solution to Problem

An aspect provides a pharmaceutical composition for preventing or treating inflammatory disease, autoimmune disease, or combinations thereof, the pharmaceutical composition including a compound represented by Formula 1, or a stereoisomer, derivative, solvate, or pharmaceutically acceptable salt thereof.

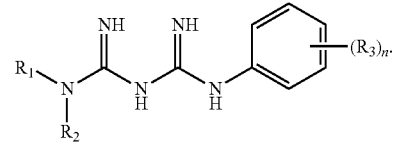

[Formula 1]

In Formula 1, $R_1$ and $R_2$ form a 3 to 8-membered heterocyclic ring, together with nitrogen connected thereto, n is an integer from 0 to 5, when $R_3$ is one or more, $R_3$ may each independently be selected from the group consisting of hydrogen, halogen, hydroxy, a $C_1$ to $C_6$ alkyl, a $C_1$ to $C_6$ alkoxy, a $C_1$ to $C_6$ alkylthio, amino, amide, sulfonamide, nitro, heteroaryl, cyano, sulfonic acid, and sulfamoyl, and $R_1$, $R_2$, and $R_3$ may each independently unsubstituted or substituted with at least one substituent selected from the group consisting of halogen, hydroxy, and a $C_1$ to $C_6$ alkyl.

The term "halogen" refers to an atom belonging to Group 7 of the Periodic Table. The halogen atom includes fluorine, chlorine, bromine, iodine, and the like.

The term "alkyl" refers to a fully saturated branched or unbranched (or linear) hydrocarbon. The alkyl may be a $C_1$ to $C_6$, $C_1$ to $C_5$, $C_1$ to $C_4$, or $C_1$ to $C_3$ alkyl group. Non-limiting examples of alkyl include methyl, ethyl, n-propyl, isopropyl, n-butyl, isobutyl, sec-butyl, n-pentyl, isopentyl, neopentyl, iso-amyl, and n-hexyl.

The term "alkoxy" refers to an alkyl linked to an oxygen atom. The $C_1$ to $C_6$ alkoxy group may be, for example, a $C_1$ to $C_6$, $C_1$ to $C_5$, $C_1$ to $C_4$, or $C_1$ to $C_3$ alkoxy group.

The term "alkylthio" refers to alkyl linked to a sulfur atom. The $C_1$ to $C_6$ alkylthio group may be, for example, a $C_1$ to $C_6$, $C_1$ to $C_5$, $C_1$ to $C_4$, or $C_1$ to $C_3$ alkylthio group.

The term "heteroaryl" refers to a monocyclic or bicyclic organic compound containing at least one heteroatom selected from the group consisting of N, O, P, and S and carbon as the remaining ring atoms. The heteroaryl group may include, for example, 1 to 5 heteroatom and a 5 to 10-membered ring member. S or N may be oxidized to have various oxidation states. Non-limiting examples of "heteroaryl" are thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, 2-pyrazine-2-yl, pyrazine-4-yl, pyrazine-5-yl, 2-pyrimidine-2-yl, 4-pyrimidine-2-yl, 5-pyrimidine-2-yl, and the like.

The term "heterocyclic ring" refers to a cyclic hydrocarbon containing at least one heteroatom. The heterocyclic ring may include, for example, a 1 to 5 hetero atoms, and a 3-membered, 4-membered, 5-membered, 6-membered, 7-membered, or 8-membered ring member. The hetero atom may be at least one selected from the group consisting of sulfur, nitrogen, oxygen and boron.

The term "substitution" refers to a case in which at least one hydrogen atom in an organic compound is substituted with other atomic groups to form a derivative, that is, the other atomic groups are introduced instead of the hydrogen atom to the organic compound, and the term "substituent" refers to the introduced atomic group.

$R_1$ and $R_2$ may form a 3 to 8-membered heterocyclic ring together with nitrogen linked thereto. The heterocyclic ring may be a 4- to 7-membered nitrogen-containing heterocyclic ring. The heterocyclic ring may be a 5-membered nitrogen-containing heterocyclic ring. The nitrogen may be from 1 to 3 nitrogen atoms. The heterocyclic ring may be, for example, pyrrolidine, azetidine, piperidine, morpholine, piperazine, azepanyl, and aziridine.

n may be an integer from 0 to 5. n may be an integer from 0 to 3. n may be 0, 1, 2, 3, 4, or 5.

When $R_3$ is one or more, $R_3$ may each independently be selected from the group consisting of hydrogen, halogen, hydroxy, a $C_1$ to $C_6$ alkyl, a $C_1$ to $C_6$ alkoxy, a $C_1$ to $C_6$ alkylthio, amino, amide, sulfonamide, nitro, heteroaryl, cyano, sulfonic acid, and sulfamoyl. When $R_3$ is one or more, $R_3$ may each independently be selected from the group consisting of hydrogen, halogen, hydroxy, a $C_1$ to $C_6$ alkyl, a $C_1$ to $C_6$ alkoxy, and heteroaryl.

$R_1$, $R_2$, and $R_3$ may each independently unsubstituted or substituted with at least one substituent selected from the group consisting of halogen, hydroxy, and a $C_1$ to $C_6$ alkyl. $R_3$ may be substituted with at least one selected from the group consisting of halogen, hydroxy, and a $C_1$ to $C_6$ alkyl. $R_3$ may be substituted with one, two, or three halogen(s). $R_3$ may be, for example, a trifluoromethyl group or a trifluoromethoxy group.

The compound of Formula 1 may be N1-piperidine-N5-(3-bromo)phenylbiguanide; N1-piperidine-N5-phenyl biguanide; N1-piperidine-N5-(3-methyl)phenyl biguanide; N1-piperidine-N5-(3-ethyl)phenyl biguanide; N1-piperidine-N5-(3-hydroxy)phenyl biguanide; N1-piperidine-N5-(3-hydroxymethyl)phenyl biguanide; N1-piperidine-N5-(3-methoxy)phenyl biguanide; N1-piperidine-N5-(4-fluoro) phenyl biguanide; N1-piperidine-N5-(2-fluoro)phenyl biguanide; N1-piperidine-N5-(3-fluoro)phenyl biguanide; N1-pyrrolidine-N5-(4-chloro)phenyl biguanide; N1-piperidine-N5-(4-chloro)phenyl biguanide; N1-pyrrolidine-N5-(3-chloro)phenyl biguanide; N1-piperidine-N5-(3-chloro) phenyl biguanide; N1-azepane-N5-(3-chloro)phenyl biguanide; N1-morpholine-N5-(3-bromo)phenyl biguanide; N1-pyrrolidine-N5-(3-trifluoromethyl)phenyl biguanide; N1-piperidine-N5-(3-trifluoromethyl)phenyl biguanide; N1-azetidine-N5-(4-trifluoromethyl)phenyl biguanide; N1-pyrrolidine-N5-(4-trifluoromethyl)phenyl biguanide; N1-piperidine-N5-(4-trifluoromethyl)phenyl biguanide; N1-pyrrolidine-N5-(3-trifluoromethoxy)phenyl biguanide; N1-piperidine-N5-(3-trifluoromethoxy)phenyl biguanide; N1-piperidine-N5-(3-difluoromethoxy)phenyl biguanide; N1-azetidine-N5-(4-trifluoromethoxy)phenyl biguanide; N1-pyrrolidine-N5-(4-trifluoromethoxy)phenyl biguanide; N1-piperidine-N5-(4-trifluoromethoxy)phenyl biguanide; N1-morpholine-N5-(4-trifluoromethoxy)phenyl biguanide; N1-(4-methyl)piperazine-N5-(4-trifluoromethoxy)phenyl biguanide; N1-piperidine-N5-(3-amino)phenyl biguanide; N1-piperidine-N5-(4-dimethylamino)phenyl biguanide; N1-piperidine-N5-(4-acetamide)phenyl biguanide; N1-piperidine-N5-(3-acetamide)phenyl biguanide; N1-piperidine-N5-(4-(1H-tetrazol-5-yl))phenyl biguanide; N1-piperidine-N5-(3-methylsulfonamide)phenyl biguanide; N1-piperidine-N5-(4-sulfonic acid)phenyl biguanide; N1-piperidine-N5-(4-methylthio)phenyl biguanide; N1-piperidine-N5-(4-sulfamoyl)phenyl biguanide; N1-piperidine-N5-(3,5-dimethoxy)phenyl biguanide; N1-piperidine-N5-(4-fluoro-3-trifluoromethyl)phenyl biguanide; N1-piperidine-N5-(4-chloro-3-trifluoromethyl)phenyl biguanide; N1-pyrrolidine-N5-(3-fluoro-4-trifluoromethyl) phenyl biguanide; N1-piperidine-N5-(3-fluoro-4-trifluoromethyl)phenyl biguanide; N1-piperidine-N5-(4-fluoro-3-trifluoromethoxy)phenyl biguanide; N1-piperidine-N5-(4-chloro-3-trifluoromethoxy)phenyl biguanide; N1-azetidine-N5-(3-fluoro-4-trifluoromethoxy)phenyl biguanide; N1-pyrrolidine-N5-(3-fluoro-4-trifluoromethoxy)phenyl biguanide; N1-piperidine-N5-(3-fluoro-4-trifluoromethoxy) phenyl biguanide; N1-azetidine-N5-(3-chloro-4-trifluoromethoxy)phenyl biguanide; N1-pyrrolidine-N5-(3-chloro-4-trifluoromethoxy)phenyl biguanide; N1-piperidine-N5-(3-chloro-4-trifluoromethoxy)phenyl biguanide; N1-piperidine-N5-(2,4-difluoro)phenyl biguanide; N1-piperidine-N5-(3,4-difluoro)phenyl biguanide; N1-piperidine-N5-(3,5-difluoro)phenyl biguanide; N1-piperidine-N5-(3,5-dichloro)phenyl biguanide; N1-piperidine-N5-(2,4-dichloro)phenyl biguanide; N1-pyrrolidine-N5-(3,4-dichloro)phenyl biguanide; N1-piperidine-N5-(3,4-dichloro)phenyl biguanide; N1-piperidine-N5-(3-chloro-5-trifluoromethoxy)phenyl biguanide; N1-pyrrolidine-N5-(3-bromo-5-trifluoromethoxy)phenyl biguanide; N1-piperidine-N5-(3-bromo-5-trifluoromethoxy)phenyl biguanide; N1-piperidine-N5-(3,4,5-trifluoro)phenyl biguanide; or N1-piperidine-N5-(2,4,6-trifluoro)phenyl biguanide.

The compound of Formula 1 may be N1-pyrrolidine-N5-(4-trifluoromethoxy)phenyl biguanide, N1-pyrrolidine-N5-(4-trifluoromethyl)phenyl biguanide, N1-piperidine-N5-(4-fluoro)phenyl biguanide, N1-piperidine-N5-(4-(1H-tetrazole-5-yl))phenyl biguanide, N1-pyrrolidine-N5-(3,4-dichloro)phenyl biguanide, or N1-piperidine-N5-(3,5-dimethoxy)phenyl biguanide.

The compound of Formula 1 may be any one of compounds represented by Formulae 2 to 7.

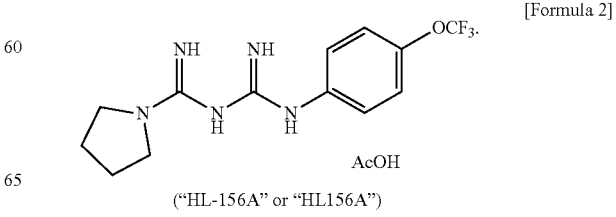

[Formula 2]

("HL-156A" or "HL156A")

-continued

[Formula 3]

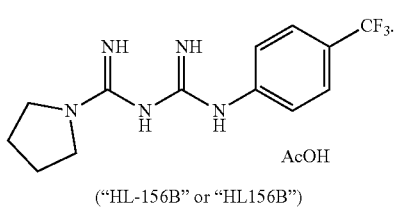

("HL-156B" or "HL156B")

[Formula 4]

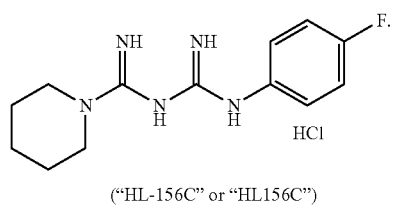

("HL-156C" or "HL156C")

[Formula 5]

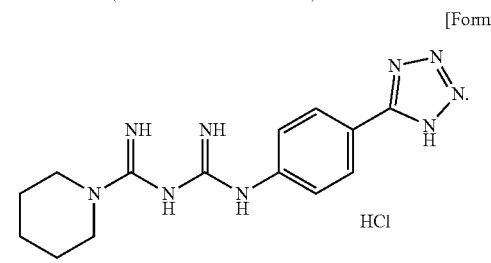

("HL-156D" or "HL156D")

[Formula 6]

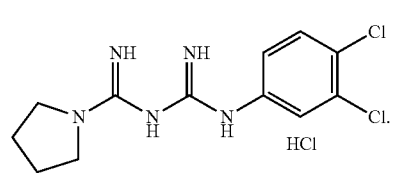

("HL-156E" or "HL156E")

[Formula 7]

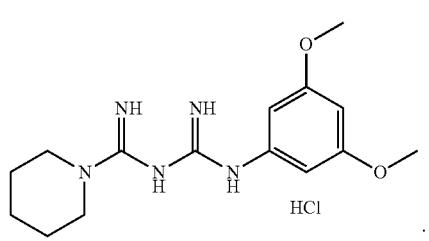

("HL-156F" or "HL156F")

The term "stereoisomer" refers to compounds that have the same molecular formula and constituting atoms which are linked in the same manner but different spatial arrangement of their atoms. The stereoisomer may be a diasteromer or an enantiomer. The enantiomer refers to an isomer that does not overlap a mirror image thereof like the relation between a right hand and a left hand, and is also called an optical isomer. The enantiomer is categorized as R (Rectus: a clockwise direction) and S (sinister: an anti-clockwise direction), when 4 or more substituents are different from each other at the chiral central carbon. The diastereoisomer refers to a stereoisomer that does not have a mirror-image relationship, and is categorized as a cis isomer and a trans isomer according to the atomic spatial arrangement.

The term "derivative" refers to a compound obtained by replacing part of the structure of the compound with other atoms or other atomic groups.

The term "solvate" refers to a compound solvated in an organic or inorganic solvent. The solvate may be, for example, a hydrate.

The term "salt" of the "pharmaceutically acceptable salt" refers to an addition salt of an inorganic acid salt, organic acid salt, or metal salt of a compound. The pharmaceutically acceptable salt may be a salt that does not cause serious irritation to the organism to which a compound is administered and does not impair the biological activity and properties of the compound. The inorganic acid salt may be hydrochloride, bromate, phosphate, sulfate, or disulfide. The organic acid salt may be a formate, an acetate, a propionate, a lactate, an oxalate, a tartrate, a malate, a maleate, a citrate, a fumarate, a besylate, a camsilate, an edisylate, a trichloroacetic acid, a trifluoroacetate, a benzoate, a gluconate, a methansulfonate, a glycolate, a succinate, a 4-toluenesulfonate, a galacturonate, an embonate, a glutamate, a methansulfonic acid, an ethanesulfonic acid, a benzenesulfonic acid, a p-toluenesulfonic acid, or an aspartate. The metal salt may be a calcium salt, a sodium salt, a magnesium salt, a strontium salt, or a potassium salt. The pharmaceutically acceptable salt may be, for example, an acetate or a hydrochloride.

The term "inflammation" of the "inflammatory disease" refers to one of the biological reactions to harmful stimulants in living tissues, for example, pathogenic microorganisms, damaged cells, stimulants and the like. Inflammation can be caused by a variety of causes, such as infection by microorganisms or injuries, surgery, burns, frostbite, electrical stimulation, and chemicals. The inflammatory disease refers to a disease that involves inflammation as a major lesion. The Inflammatory disease may be, selected from the group consisting of sepsis, gastritis, enteritis, nephritis, hepatitis, chronic obstructive pulmonary disease (COPD), pulmonary fibrosis, hypersensitivity colorectal syndrome, inflammatory pain, migraine, headaches, back pain, fibromyalgia, fascial disease, viral infection, bacterial infection, fungal infection, burns, wounds due to surgical or dental surgery, prostaglandin excessive syndrome, atherosclerosis, gout, Hodgkin's disease, pancreatitis, conjunctivitis, iritis, sclerotitis, uveitis, and eczema.

The term "autoimmune disease" refers to a disease in which an immune-function abnormality occurs, resulting in immune cells in the body attacking organs or tissues of the body. The autoimmune disease can be categorized as a disease associated with organ-specific autoantibodies and an organ non-specific (systemic) disease. The autoimmune disease may be selected from the group consisting of hemophagocytic lymphohistiocytosis, systemic lupus erythematosus, Kikuchi disease, vasculitis, adult onset Still's disease, rheumatoid arthritis, inflammatory myositis, Behcet disease, IgG4-related disease, Sjogren syndrome, giant cell arteritis, temporal arteritis, Type 1 diabetes, atopic dermatitis, Crohn's disease, systemic sclerosis, psoriasis, multiple sclerosis, and Graves hyperthyroidism.

The compound of Formula 1, and the stereoisomer, derivative, solvate, or pharmaceutically acceptable salt thereof may inhibit the differentiation or proliferation of a memory T cell. The memory T cell may be a central memory T cell ($T_{CM}$), or an effector memory T cell ($T_{EM}$). The compound of Formula 1, and the stereoisomer, derivative, solvate, or pharmaceutically acceptable salt thereof may promote the differentiation or proliferation of the effector T cell ($T_{EFF}$). TCM may express CD127 protein and CD62L protein. $T_{EM}$ may express CD127 protein, but may not express CD62L protein. $T_{EFF}$ may not express CD127 protein and CD62L protein.

The term "prevention" refers to any action that inhibits the development of, or delays the onset of inflammatory disease, autoimmune disease, or combinations thereof by the administration of the pharmaceutical composition. The term "treatment" refers to any action that alleviates or advantageously alters the symptoms of inflammatory disease, autoimmune disease, or combinations thereof by the administration of the pharmaceutical composition.

The pharmaceutical composition may include a pharmaceutically acceptable carrier. The carrier is used herein to include an excipient, a diluent, or an adjuvant. The carrier may be, for example, selected from the group consisting of lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinylpyrrolidone, water, physiological saline, a buffer such as PBS, methyl hydroxybenzoate, propyl hydroxybenzoate, talc, magnesium stearate, and mineral oil. The pharmaceutical composition may include fillers, anticoagulants, lubricants, wetting agents, flavors, emulsifiers, preservatives, or combinations thereof.

The pharmaceutical composition may be prepared in any formulation according to methods of the related art. The pharmaceutical composition may be formulated as, for example, an oral dosage form (powder, tablet, capsule, syrup, pill, or granule), or a parenteral formulation (for example, an injection). In addition, the pharmaceutical composition may be formulated as a systemic formulation or as a topical formulation.

The pharmaceutical composition may further include an immunosuppressive agent. The term "immunosuppressive drug" refers to a substance that inhibits immune functions. The immunosuppressive drug may glucocorticoid, a cell proliferation inhibitor, an antibody or antigen-binding fragment, a drug acting on immunophilin, and the like. The cell proliferation inhibitor may be an alkylating agent, an antimetabolite (for example, methotrexate, azathioprine, mercaptopurine, and fluorouracil), or the like. The antibody or antigen-binding fragment may be, for example, an antibody or antigen-binding fragment that binds specifically to a T-cell receptor or a IL-2 receptor. The drug acting on immunophilin may be, for example, ciclosporin, tacrolimus, rapamycin, and everolimus. The immunosuppressive drug may include interferon, opioid, a tumor necrosis factor (TNF) binding protein, mycophenolate, or the like. The immunosuppressive drug may be, for example, rapamycin. The pharmaceutical composition may be a single composition or separate compositions.

The pharmaceutical composition may include the compound of Formula 1, or the stereoisomer, derivative, solvate, or pharmaceutically acceptable salt thereof in an effective amount. The term "effective amount" refers to an amount sufficient to show the effect of prevention or treatment when administered to a subject in need of such prevention or treatment. The effective amount may be appropriately determined by ordinary skilled in the art according to the subject. The effective amount may depend on the severity of the disease, the age, body weight, health conditions, and gender of the patient, sensitivity to the drug, administration hours, route of administration and rate of excretion of the patient, duration of treatment, a combination with the used composition, or drugs simultaneously used with the composition, and other factors that are known in the medical field. The effective amount may be, based on the amount of the pharmaceutical composition, in the range of about 0.5 µg to about 2 g, about 1 µg to about 1 g, about 10 µg to about 500 mg, about 100 µg to about 100 mg, or about 1 mg to about 50 mg.

The pharmaceutical composition may be administered in a conventional manner via oral, transdermal, subcutaneous, rectal, intravenous, intraarterial, intraperitoneal, intramuscular, intrasternal, topical, or intradermal routes. The dosage of the pharmaceutical composition may be, for example, based on an adult, in the range of about 0.001 mg/kg to about 100 mg/kg, about 0.01 mg/kg to about 10 mg/kg, or about 0.1 mg/kg to about 1 mg/kg. The administration may be performed once a day, multiple times a day, once a week, once every two weeks, once every three weeks, or once every four weeks to once a year.

Another aspect provides a method of preventing or treating inflammatory disease, autoimmune disease, or combinations thereof, the method including administering, to a subject, the compound of Formula 1, or the stereoisomer, derivative, solvate, or pharmaceutically acceptable salt thereof.

The method includes administering, to a subject, the compound of Formula 1, or the stereoisomer, derivative, solvate, or pharmaceutically acceptable salt thereof.

The compound of Formula 1, the stereoisomer, the derivative, the solvate, pharmaceutically acceptable salt, the inflammatory disease, the autoimmune disease, the prevention, and the treatment are the same as described above.

The subject may be mammals, for example, humans, cows, horses, pigs, dogs, sheep, goats, or cats. The subject may be suffering from, or at risk of, inflammatory disease, autoimmune disease, or combinations thereof.

The method may further include administering an immunosuppressive drug to the subject. The immunosuppressive drug may be administered simultaneously, separately, or sequentially with the compound of Formula 1, or the stereoisomer, derivative, solvate, or pharmaceutically acceptable salt thereof.

The administering may be performed via oral or parenteral routes. The administering may be performed via, for example, oral, transdermal, subcutaneous, rectal, intravenous, intraarterial, intraperitoneal, intramuscular, intrasternal, topical, intranasal, intratracheal, or intradermal routes. The pharmaceutical composition may be administered systemically or topically and may be administered alone or in combination with other pharmaceutically active compounds.

The dosage of the compound of Formula 1, or the stereoisomer, derivative, solvate, or pharmaceutically acceptable salt thereof may depend on the conditions and body weight of the patient, the severity of the disease, the formulation of the drug, and the administration route and period. However, the dosage may be appropriately determined by a person skilled in the art.

The dosage may be, for example, based on an adult, in the range of about 0.001 mg/kg to about 100 mg/kg, about 0.01 mg/kg to about 10 mg/kg, or about 0.1 mg/kg to about 1 mg/kg. The administration may be performed once a day, multiple times a day, once a week, once every two weeks, once every three weeks, or once every four weeks to once a year.

Advantageous Effects of Disclosure

The pharmaceutical composition including the compound of Formula 1, or the stereoisomer, derivative, solvate, or pharmaceutically acceptable salt thereof according to an aspect and the method using the pharmaceutical composition according to another aspect can be used to effectively prevent or treat inflammatory disease, autoimmune disease, or combinations thereof.

MODE OF DISCLOSURE

This disclosure will be described in detail with reference to the following Examples. However, these Examples are provided herein to illustrate one or more detailed examples, and the scope of the present disclosure is not limited to these Examples.

Example 1. Identification of the Effect of HL-156 Compound on Inflammation and Autoimmune Disease 1. Effect of HL-156 Compound on T Cell Activation In Vitro The spleen was harvested from normal C57BL/6 mice (Orient Bio) and the mixture obtained by adding a RPMI solution containing 2% (v/v) fetal bovine serum (FBS) to the spleen tissues was homogenized by using a 40 μm strainer.

T cells were isolated from the homogenized spleen tissue by using CD90.2 magnetic beads (Miltenyi Biotec). Isolated T cells were labeled using CellTrace™ Violet (CTV). Subsequently, labeled T cells were activated for 3 days by using anti-CD3/28 Dynabeads®.

During T cells were activated, 5 μM, 15 μM, 45 μM, or 135 μM HL-156A (Hanoi BioPharma Inc.), and/or 20 nM rapamycin (LC Laboratories) were added to identify the effect of HL-156A, or the combination of HL-156A and rapamycin on the proliferation of T cells. As a negative control, PBS supplemented with 5% (v/v) DMSO was used. As a comparative control, 20 nM rapamycin or 2 mM metformin (Hanoi BioPharma Inc.)-added T cells was used.

Activated T cells were immunostained by using allophycocyanin (APC)-labeled anti-CD4 antibody (BD Biosciences) and peridinin chlorophyll protein complex (PerCP)-labeled anti-CD8 antibody (eBioscience). Immunostained T cells were analyzed by flow cytometric analysis to identify the surface molecular phenotype thereof. From the results obtained by flow cytometric analysis, the proliferation ratio (%) of the T cell with respect to a material treated on the T cell was calculated, and the proliferation ratio (%) of CD4 T cell and the proliferation ratio (%) of CD8 T cell with respect to a compound are shown in FIGS. 1A and 1B, respectively.

Figure 1A:
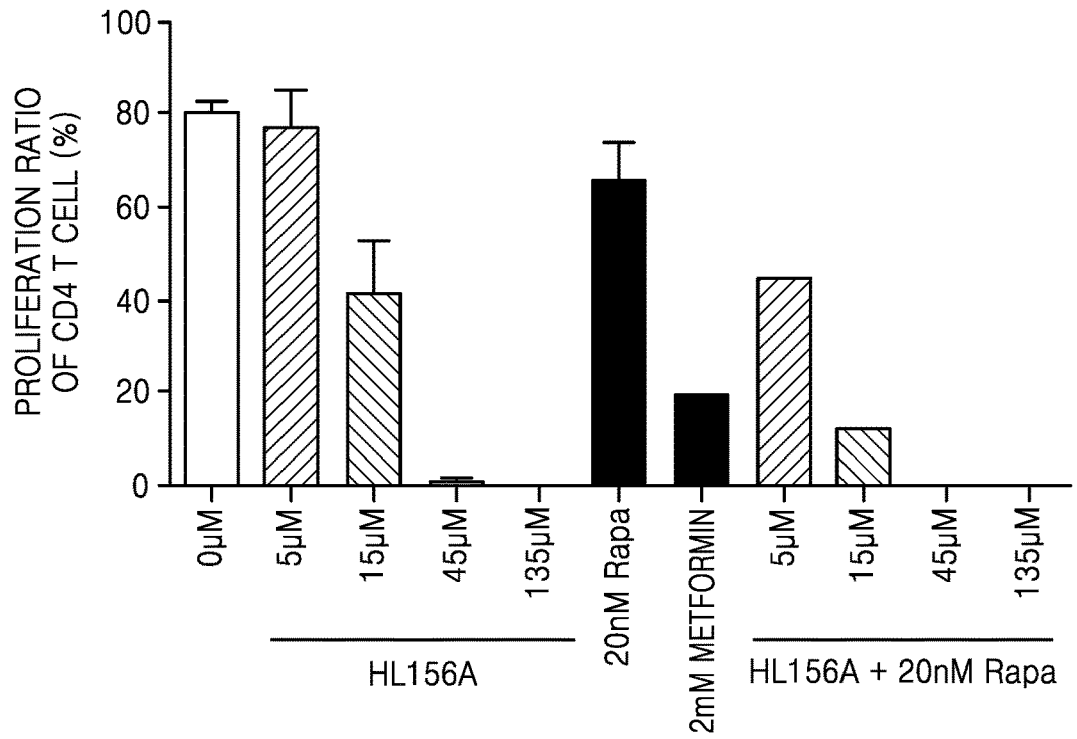
FIGS. 1A and 1B show graphs of a proliferation ratio of a CD4 T cell (%) and a proliferation ratio of a CD8 T cell (%) with respect to HL-156A, rapamycin, metformin, or a combination thereof, respectively (error bar: 95% confidence interval, Rapa: rapamycin).
Figure 1B:
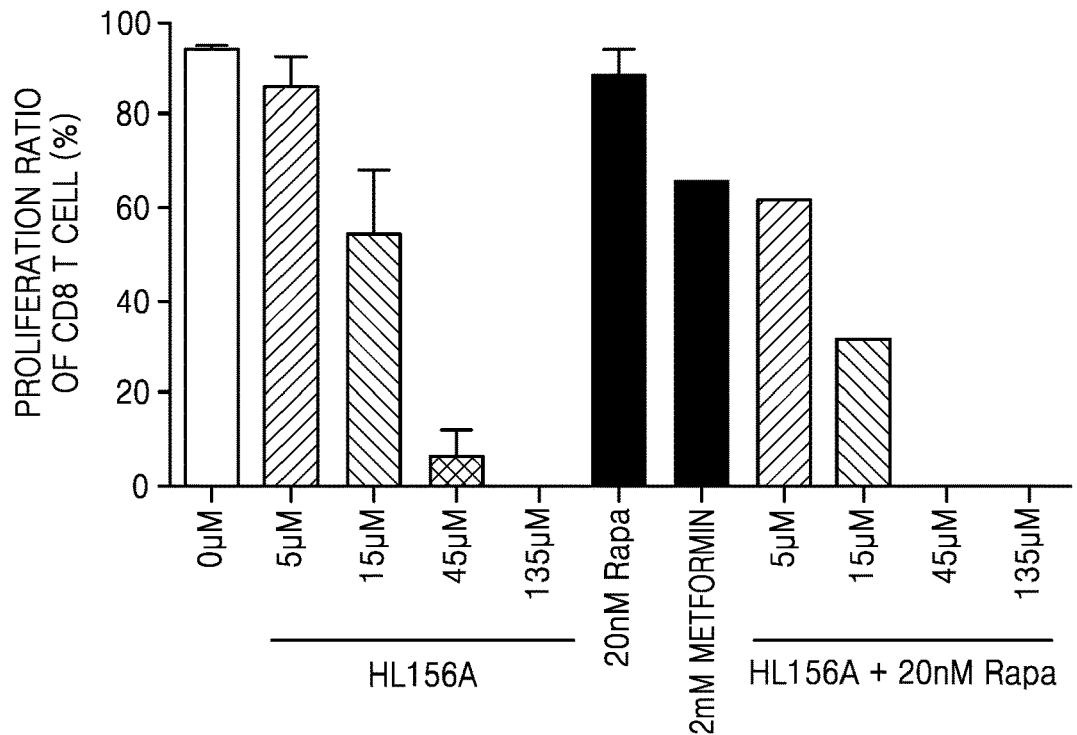

As shown in FIGS. 1A and 1B, HL-156A significantly inhibited the proliferation of CD4 T cell and CD8 T cell in proportion to the concentration. In addition, the combination of HL-156A and rapamycin inhibited the proliferation of T cells compared with when HL-156A and rapamycin were used separately. This result identifies that the combination of HL-156A and rapamycin has a synergistic effect.

2. Effect of HL-156 Compound on the Production of Inflammatory Factors

1) Inhibition of Tumor Necrosis Factor-Alpha Production in THP-1 Cell Line

The human THP-1 cell line (ATCC) was prepared and cultured at a temperature of 37° C. and under 5% $CO_2$.

Prepared THP-1 cells were inoculated onto a 96-well plate at the density of 1×10$^5$, and HL-156A, HL-156B, HL-156C, HL-156D, HL-156E, and HL-156F (all produced by Hanoi BioPharma Inc.) were added at the concentration of 1 μM or 10 μM to the cell culture solution. Thereafter, 25 ng/ml of phorbol 12-myristate 13-acetate (PMA, Sigma-Aldrich) was added to the cell culture solution, and cells were cultured for 24 hours, and then, lipopolysaccharide (LPS) was added thereto to induce an immune response of THP-1 cell. As a negative control, a group in which LPS was not added or a group in which LPS was added but no drug was added, were used.

THP-1 cells were cultured for 24 hours, and then, the amount of tumor necrosis factor-alpha (TNF-α) in the culture solution by using TNF ELISA kit (Invitrogen) was measured. The amount (pg/ml) of TNF-α produced in THP-1 cells according to the administered drug is shown in FIG. 2A and Table 1.

TABLE 1

| Administered group | Average | Standard deviation | Standard error | p-value (t-test) |
|---|---|---|---|---|
| No LPS | 0 | 0 | 0 | |
| No Drug | 5250 | 483.5 | 279.1 | |
| HL-156A 10 μM | 3025 | 377.2 | 217.8 | 0.045 |
| HL-156A 1 μM | 6750 | 330.3 | 190.7 | |
| HL-156B 10 μM | 2875 | 130.3 | 75.22 | 0.007 |
| HL-156B 1 μM | 6125 | 662.9 | 382.7 | |
| HL-156C 10 μM | 6375 | 904 | 521.9 | |
| HL-156C 1 μM | 4825 | 1517 | 875.6 | |
| HL-156D 10 μM | 5150 | 621.9 | 359 | |
| HL-156D 1 μM | 6125 | 377.2 | 217.8 | |
| HL-156E 10 μM | 1925 | 238.5 | 137.7 | 0.001 |
| HL-156E 1 μM | 4725 | 735.5 | 424.6 | |
| HL-156F 10 μM | 4650 | 310.5 | 179.3 | 0.026 |
| HL-156F 1 μM | 6425 | 635.8 | 367.1 | |

Figure 2A:
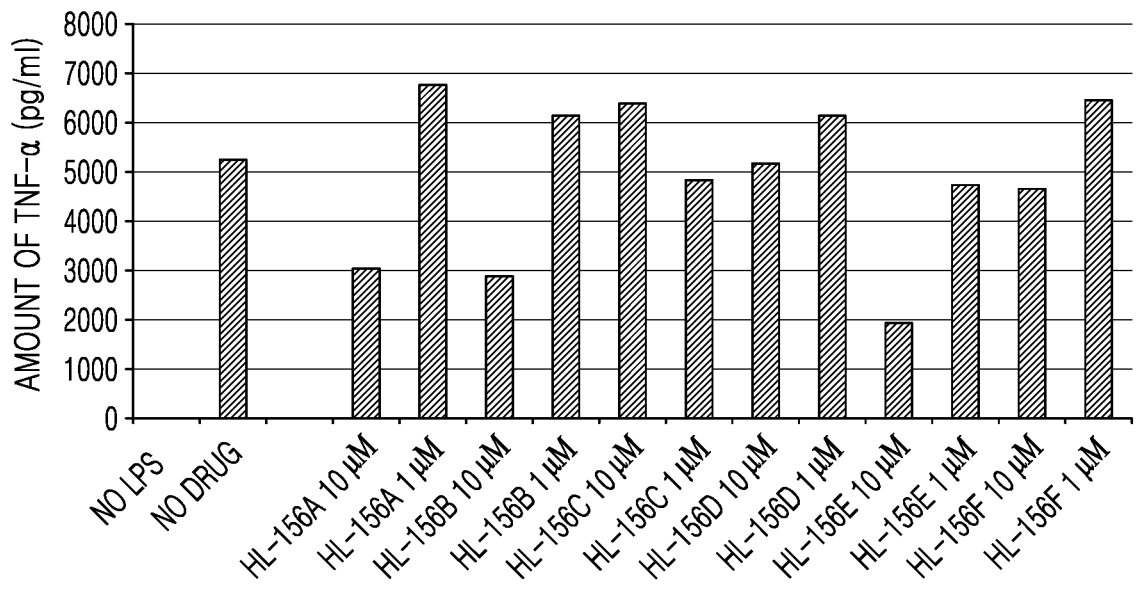
FIG. 2A shows a graph of the amount of TNF-α (μg/ml) produced in a THP-1 cell according to the administration of HL-156A, HL-156B, HL-156C, HL-156D, HL-156E, and HL-156F.

* p-value is a student t-test which was compared with the group which was not administered with drug As shown in FIG. 2A and Table 1, HL-156A, HL-156B, HL-156E, and HL-156F inhibited the production of TNF-α in cells. Since TNF-α is a cytokine associated with systemic inflammation and acts to regulate immune cells, it was confirmed that HL-156 compound could inhibit the inflammatory response.

2) Inhibition of Tumor Necrosis Factor-Alpha Production in Synoviocyte

Human synoviocyte cell line MH7A (provided by Prof. Kim Wan-wook of Catholic University) was prepared and cultured at a temperature of 37° C. and under 5% $CO_2$.

The prepared MH7A cells were inoculated onto a 96-well plate at the density of $3 \times 10^4$ cells, and lipopolysaccharide (LPS) was added thereto to induce the immune response of MH7A cells. Then, HL-156A or HL-156B was added at a concentration of 0.1 µM, 1 µM, or 10 µM to the cell culture solution. As a negative control, a group in which LPS was used but no drug was used, was used.

After MH7A cells were cultured for 24 hours, the amount of TNF-α in the culture solution was measured by using a TNF-α ELISA kit (Peprotach). Table 2 shows the amount of TNF-α according to the administration of drug, and FIG. 2B shows a graph of the amount of TNF-α (µg/ml) produced in MH7A cells when HL-156A or HL-156B was administered.

TABLE 2

| Administered group | Average | Standard deviation | Standard error | p-value (t-test) |
|---|---|---|---|---|
| TNF-α control | 1 | 0.19 | 0.1097 | |
| TNF-α HL156A 0.1 µM | 0.82 | 0.09539 | 0.05508 | NS |
| TNF-α HL156A 1 µM | 0.75 | 0.04583 | 0.02646 | NS |
| TNF-α HL156A 10 µM | 0.72 | 0.03606 | 0.02082 | NS |
| TNF-α control | 3.53 | 0.2358 | 0.1361 | |
| TNF-α HL156B 0.1 µM | 3.11 | 0.2088 | 0.1206 | NS |
| TNF-α HL156B 1 µM | 2.56 | 0.291 | 0.168 | 0.0068 |
| TNF-α HL156B 10 µM | 2.17 | 0.1389 | 0.08021 | 0.0099 |

Figure 2B:
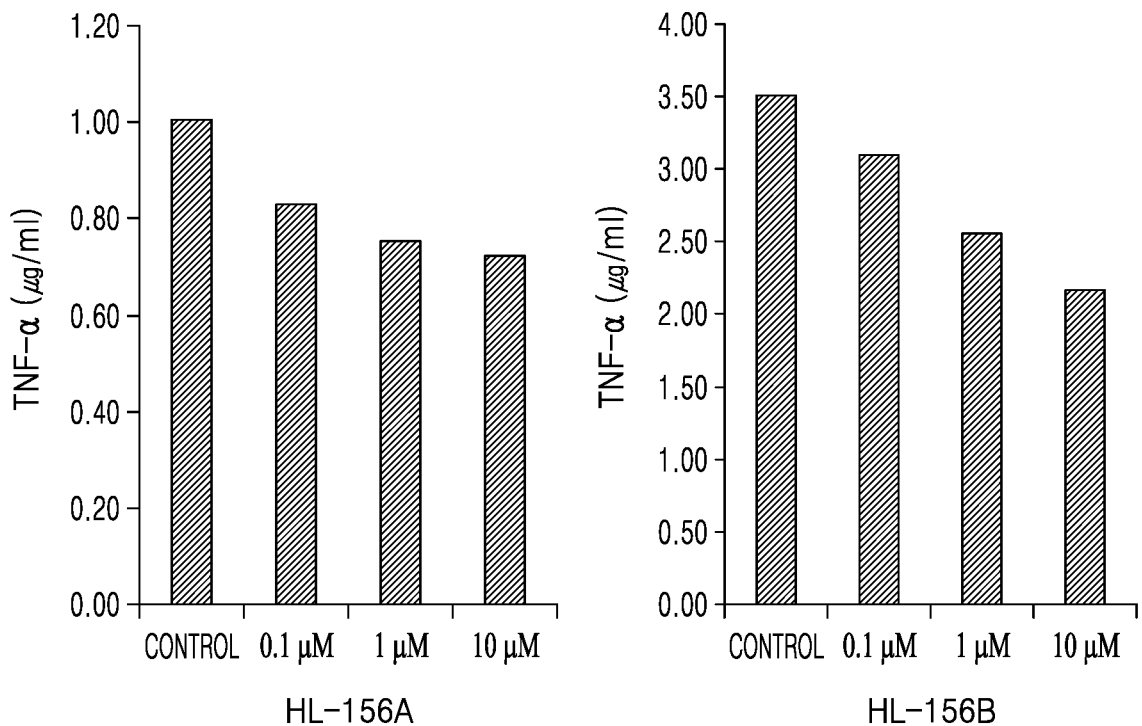
FIG. 2B shows a graph of the amount of TNF-α (μg/ml) produced in MH7A cells according to the administration of HL-156A or HL-156B.

* p-value is a student t-test obtained by comparing each of groups administered with drugs with a control.
* NS: not significant As shown in Table 2 and FIG. 2B, HL-156A and HL-156B inhibited the production of TNF-α in a concentration-dependent manner in the cells. Therefore, it was confirmed that HL-156 compound can inhibit inflammatory reaction or prevent or treat arthritis in the synovial membrane cells.

3. Effect of HL-156 Compound on T Cell Activation In Vivo $2 \times 10^5$ pfu (plaque forming unit) of lymphocytic choriomeningitis virus (LCMV) Armstrong cell line (Emory University School of Medicine) was injected intraperitoneally into normal C57BL/6 mouse (Orient Bio) (day 0).

Figure 3:
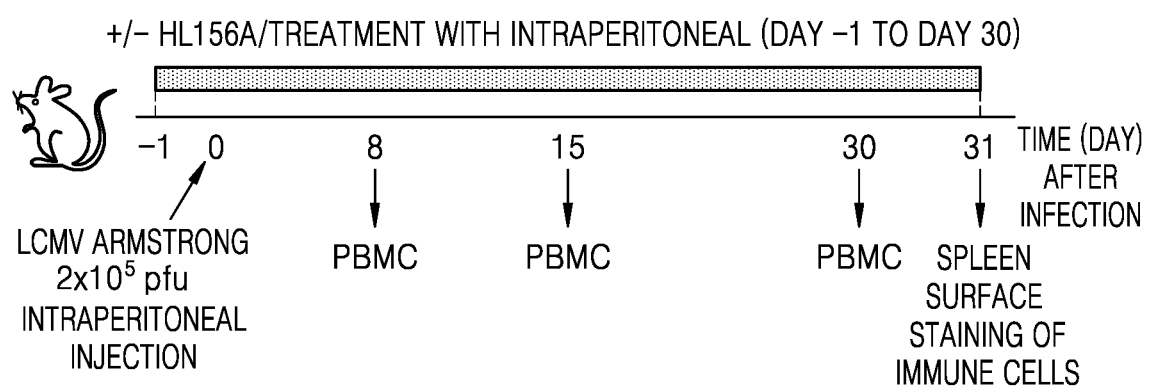
FIG. 3 shows a schematic diagram illustrating a process of administering, to a mouse, HL-156A, or a combination of HL-156A and rapamycin.

The mouse was administered with HL-156A every other day at a dosage of 5 mg/kg body weight or 20 mg/kg body weight. Also, in a group administered with rapamycin, rapamycin was administered to the mouse at a dosage of 75 µg/kg body weight on a daily basis. In a group administered with HL-156A and rapamycin, the mouse was administered with HL-156A at a dosage of 5 mg/kg body weight once every two days, and administered with rapamycin at a dosage of 75 µg/kg body weight daily. As a negative control, PBS supplemented with 5% (v/v) DMSO was used. HL-156A or rapamycin was intraperitoneally injected from the day before the administration of the LCMV Armstrong strain (day −1) to the 30th day after the administration. The peripheral blood mononuclear cells (PBMC) of the mouse were obtained by collecting blood at the 8th, 15th, and 30th days after the viral injection. On day 31, the mouse was sacrificed, and the spleen of the mice was harvested as described in Example 1.1. CD8 T cell expressing antigen gp33, specific to LMCV, (GP33+CD8 T cell) was isolated from the spleen tissue by using anti-GP33 antibody. FIG. 3 shows a schematic diagram illustrating a process of administering, to a mouse, HL-156A, or a combination of HL-156A and rapamycin.

Figure 4A:
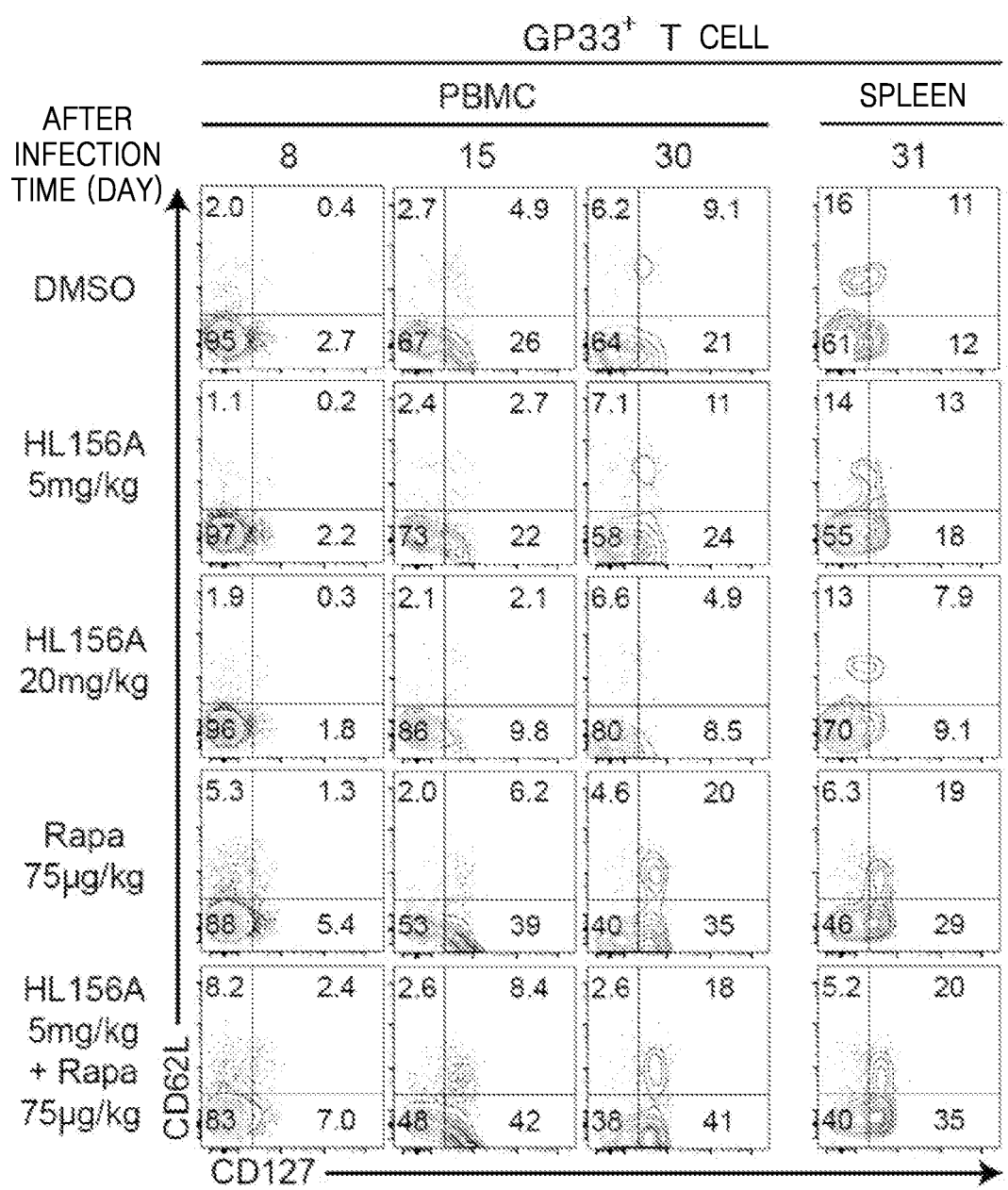
FIG. 4A shows a graph showing results obtained by flow cytometric analysis.

As described in Example 1.1, isolated GP33+CD8 T cells were immunostained by using phycoerythrin (PE)-labeled anti-CD127 antibody (eBioscience) and fluorescein isothiocyanate (FITC)-labeled anti-CD62L antibody (BioLegend), and the surface molecular phenotype of T cells was analyzed by flow cytometry. From results obtained by flow cytometric analysis, the change in differentiation of virus-specific CD8+ T cell over time after the viral infection when HL-156A, or the combination of HL-156A and rapamycin was administered, was confirmed, and shown in FIG. 4A.

Figure 4B:
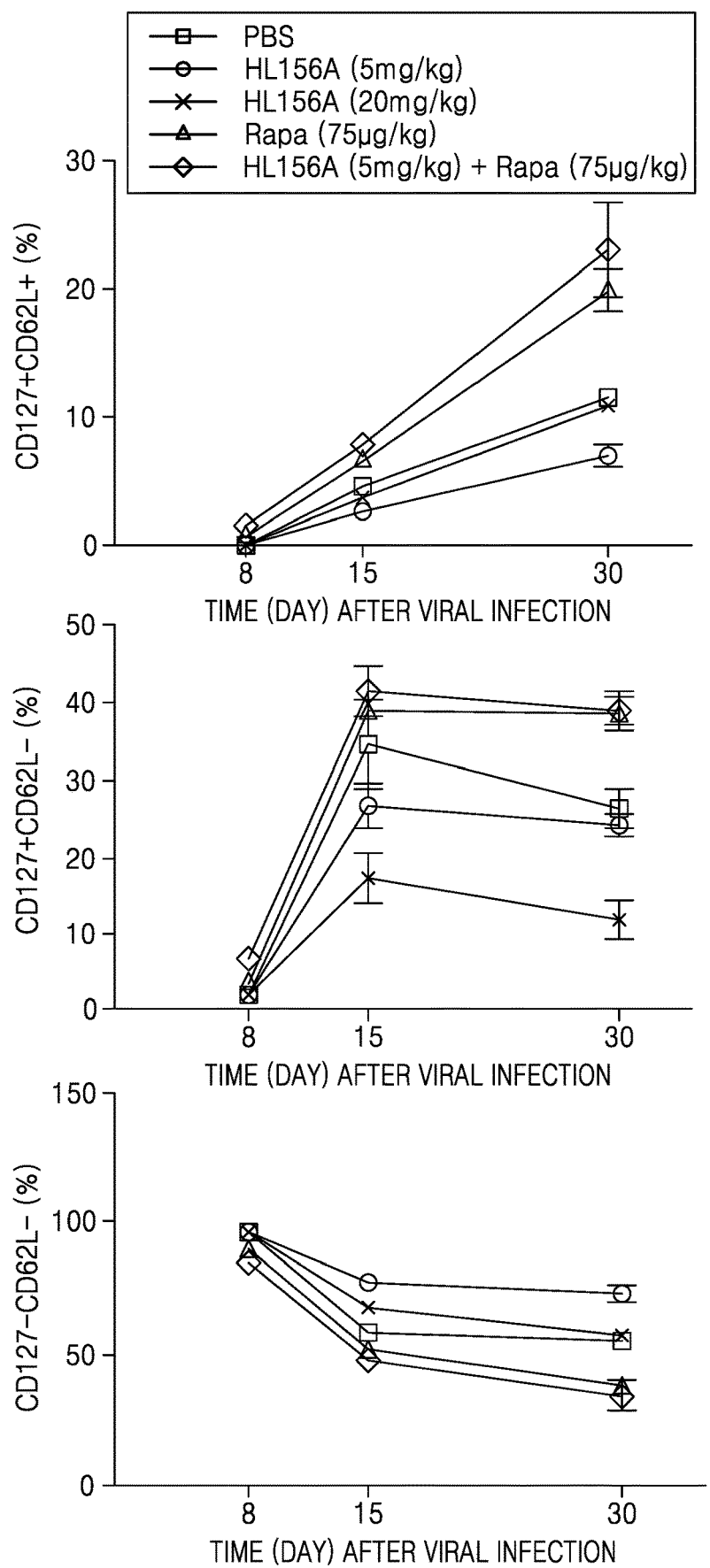
FIG. 4B shows a ratio (%) of a CD127+CD62L+ $T_{CM}$ cell, a CD127+CD62L- $T_{EM}$ cell, and a CD127-CD62L- $T_{EFF}$ cell in PBMC over time after the viral infection.
Figure 4C:
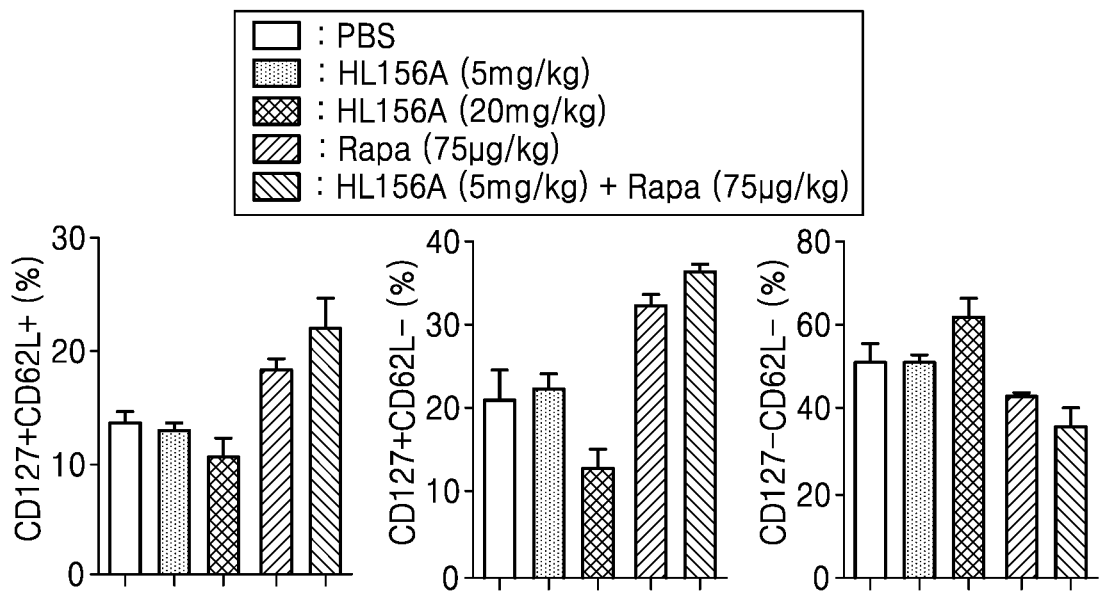
FIG. 4C shows a ratio (%) of a CD127+CD62L+$T_{CM}$ cell, a CD127+CD62L- $T_{EM}$ cell, and a CD127-CD62L-$T_{EFF}$ cell in PBMC in T cells of a spleen.

With respect to the isolated T cells, the ratio of central memory T cell ($T_{CM}$) expressing CD127 and CD62L (CD127+CD62L+), effector memory T cell ($T_{EM}$) expressing CD127 and not expressing CD62L (CD127+CD62L−), and effector T cell ($T_{EFF}$) not expressing CD127 and CD62L (CD127−CD62L−) was calculated. The ratio (%) of CD127+CD62L+ $T_{CM}$ cell, CD127+CD62L− $T_{EM}$ cell, and CD127−CD62L− $T_{EFF}$ cell in PBMC over time after the viral infection, when HL-156A, or the combination of HL-156A and rapamycin was administered, is shown in FIG. 4B. FIG. 4C shows the ratio (%) of CD127+CD62L+$T_{CM}$ cell, CD127+CD62L− $T_{EM}$ cell, and CD127−CD62L− $T_{EFF}$ cell in PBMCs in T cells of spleen on day 31.

As shown in FIGS. 4B and 4C, HL-156A inhibited the differentiation of $T_{CM}$ cells and $T_{EM}$ cells in PBMCs and promoted the proliferation of $T_{EFF}$ cells in PBMCs. On the other hand, rapamycin promoted differentiation of $T_{CM}$ cells and $T_{EM}$ cells in PBMCs and inhibited the proliferation of $T_{EFF}$ cells in PBMCs. Thus, unlike rapamycin, HL-156A inhibits the differentiation or production of memory T cells and promotes the proliferation of effector T cells. Therefore, it was confirmed that HL-156A has an effect capable of treating and preventing T cell-associated disease, for example, Inflammatory disease or autoimmune disease.

4. Therapeutic Effect of HL-156 Compound on Arthritis in Collagen-Induced Arthritis Mouse Model Bovine Type II collagen was dissolved in complete freund's adjuvant (CFA) containing 250 µg per mouse of heat-sterilized *Mycobacterium tuberculosis* H37Ra (BD Sciences) to prepare a collagen solution.

DBA/1 mouse was immunized by intradermally injecting 100 g per mouse of the prepared collagen thereinto. On day 21 after the immunization, bovine Type II collagen dissolved in incomplete freund's adjuvant (IFA) was injected subcutaneously into the tail of a mouse in an amount of 100 µg to boost the immune system.

The arthritis score of mice was measured using the following criteria:

Grade 0: swelling or erythema;
Grade 1: mild swelling and erythema, inflammation of the toes;
Grade 2: moderate swelling and erythema confined to the distal to mid-limbs;
Grade 3: extended to the ankle, clear swelling and erythema; and
Grade 4: Severe swelling, erythema, and joint stiffness of ankle, foot, and toes.

A score of 0 to 4 was assigned to each leg, and a maximum of 16 points of arthritis scores were assigned to each mouse.

Mice with an average arthritis score of 8 were randomly selected. The HL-156A compound was diluted in PBS and administered to the selected mice intraperitoneally once every two days with 60 mg/kg body weight of HL-156A compound. Thereafter, the arthritis score of the mouse was measured, and the change in arthritis score over time is shown in FIG. 5 (*: p<0.05).

Figure 5:
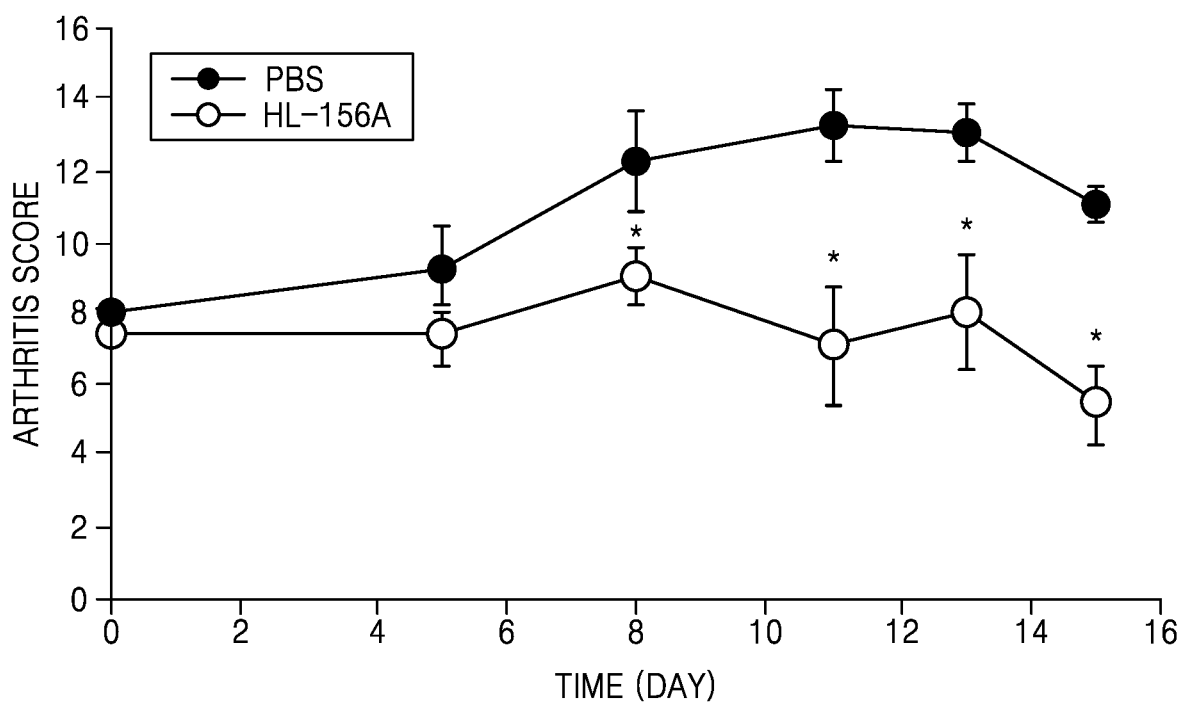
FIG. 5 shows a graph of a change in arthritis score over time in a mouse model of collagen-induced arthritis when HL-156A was administered.

As shown in FIG. 5, the HL-156A compound decreased the arthritis score over time. Therefore, it was confirmed that HL-156A compound has the effect of treating and preventing arthritis.

The invention claimed is:

1. A method of preventing or treating autoimmune disease, graft rejection responses, or combinations thereof, the method including administering, to a subject, a compound represented by Formula 1, or a stereoisomer, derivative, solvate, or pharmaceutically acceptable salt thereof:

[Formula 2]

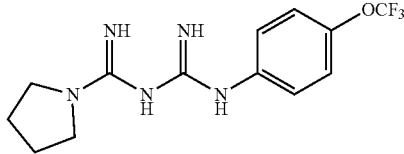

wherein the subject is suffering from, or at risk of, autoimmune disease, graft rejection responses or combinations thereof, and wherein the autoimmune disease is systemic lupus erythematosus or rheumatoid arthritis.

2. The method of claim 1, wherein the pharmaceutically acceptable salt is acetate or hydrochloride.

3. The method of claim 1, wherein the compound of Formula 2, and the stereoisomer, derivative, solvate, or pharmaceutically acceptable salt thereof inhibit the differentiation or proliferation of a memory T cell.

4. The method of claim 3, wherein the memory T cell is a central memory T cell (TCM) or an effector memory T cell (TEM).

5. The method of claim 1, wherein the compound of Formula 2, and the stereoisomer, derivative, solvate, or pharmaceutically acceptable salt thereof promote the differentiation or proliferation of the effector T cell ($T_{EFF}$).

6. The method of claim 1, further comprising administering an immunosuppressive drug to the subject.

7. The method of claim 6, wherein the immunosuppressive drug is rapamycin.

8. The method of claim 6, wherein the immunosuppressive drug is administered simultaneously, separately, or sequentially with the compound of Formula 1, or the stereoisomer, derivative, solvate, or pharmaceutically acceptable salt thereof.

* * * * *